United States Patent [19]

Cadwell

[11] Patent Number: 4,940,453
[45] Date of Patent: Jul. 10, 1990

[54] METHOD AND APPARATUS FOR MAGNETICALLY STIMULATING NEURONS

[75] Inventor: John A. Cadwell, Kennewick, Wash.

[73] Assignee: Cadwell Industries, Inc., Kennewick, Wash.

[21] Appl. No.: 8,210

[22] Filed: Jan. 28, 1987

[51] Int. Cl.$^5$ .............................................. A61B 15/05
[52] U.S. Cl. ....................................... 600/13; 600/15; 128/714
[58] Field of Search ................................... 600/13–15; 128/741

[56] References Cited

U.S. PATENT DOCUMENTS

| | | | |
|---|---|---|---|
| 2,808,826 | 10/1957 | Reiner et al. | 128/741 |
| 3,706,308 | 12/1972 | John et al. | 128/2.06 R |
| 3,841,305 | 10/1974 | Hallgren | 128/1.3 |
| 3,841,306 | 10/1974 | Hallgren | 600/13 |
| 3,901,215 | 8/1975 | John | 128/2.1 B |
| 3,915,151 | 10/1975 | Kraus | 600/13 |
| 4,244,376 | 1/1981 | Fisher et al. | 128/731 |

(List continued on next page.)

OTHER PUBLICATIONS

Maass, IEEE Transactions on Magnetics, vol. MAG-6, No. 2, Jun. 1970, pp. 322–326.
Dr. A. T. Barker et al., *An Introduction to Magnetic Stimulation of the Human Brain and Peripheral Nervous System*, Aug. 1985.

(List continued on next page.)

Primary Examiner—Francis Jaworski
Assistant Examiner—John C. Hanley
Attorney, Agent, or Firm—Christensen, O'Connor, Johnson & Kindness

[57] ABSTRACT

An efficient method and apparatus for magnetically stimulating the neural pathways of a higher level organism, namely the human body, is disclosed. The method includes selectively applying sinusoidally fluctuating electric power to a stimulator coil that overlies the neurons to be stimulated. The frequency of the power and, thus, the period of magnetic field produced by the coil is chosen to correspond to the time constant of the neurons to be stimulated. Realizable values fall in the range of 1.25 to 1.43 times the time constant of the neurons to be stimulated. The current and voltage of the applied power are in phase quadrature with the current lagging the voltage. During the first polarity (e.g., positive) excursion of the applied voltage, the magnetic field produced by the coil is insufficient to stimulate the underlying neurons, i.e., create a neuron depolarizing electric field. Rather, stimulation occurs during the second polarity (e.g., negative) excursion of the applied voltage. Preferably, coil current flow terminates at the end of the first current cycle. Alternatively, if restimulation during the third and subsequent polarity excursions of the applied voltage is desired, the coil current can be allowed to decay. The apparatus of the invention includes a series circuit comprising the stimulator coil 59 and a high voltage capacitor bank 57 connected in parallel with a power switch 55, across the output of a power supply 51. Closure of the power switch 55 results in the capacitor bank 57 being discharged through the coil 59 and the creation of the magnetic field that stimulates the underlying neurons. Efficiency is high because the resistance of both the capacitor discharge circuit and the power supply output are low. Further, because the resistance of the capacitor discharge circuit is low, discharge current flow is high, whereby an intense magnetic field is produced. Interlock circuits are provided to prevent the inadvertent operation of the apparatus. If desired, magnetic neuron stimulation can be enhanced simultaneously and/or sequentially by applying electric power to a pair of spaced-apart electrodes located in the vicinity of the coil.

21 Claims, 9 Drawing Sheets

U.S. PATENT DOCUMENTS

| | | | |
|---|---|---|---|
| 4,304,242 | 12/1981 | Siarkiewicz et al. | 128/745 |
| 4,387,723 | 6/1983 | Atlee et al. | 128/741 |
| 4,408,616 | 10/1983 | Duffy et al. | 128/731 |
| 4,417,591 | 11/1983 | Culver | 128/731 |
| 4,454,883 | 6/1984 | Fellus | 600/14 |
| 4,493,327 | 1/1985 | Bergelson et al. | 128/731 |
| 4,493,539 | 1/1985 | Cannon, Jr. | 351/205 |
| 4,498,080 | 2/1985 | Culver | 340/728 |
| 4,570,640 | 2/1986 | Barsa | 128/741 |
| 4,595,018 | 6/1986 | Rantala | 128/741 |
| 4,672,951 | 6/1987 | Welch | 600/14 |

OTHER PUBLICATIONS

A. T. Barker et al., "Magnetic Stimulation of the Human Brain," *Physiological Society*, Jul. 1985, p. 9P.

Reginald G. Bickford, M.D., F.R.C.P., *Magnetic Stimulation of the Nervous System Nerve, Cord and Brain* (Grand Rounds Handout), Jul. 25, 1986.

Reginald G. Bickford et al., "Neuronal Stimulation by Pulsed Magnetic Fields in Animals and Man," *Digest of the 6th International Conference on Medical Electronics and Biological Engineering*, Tokyo, 1965.

R. Jalinous et al., "The Design, Construction and Performance of a Magnetic Nerve Stimulator," *IEE International Conference on Electric and Magnetic Fields in Medicine and Biology*, Dec. 1985, pp. 59–63.

"Non-Invasive Magnetic Stimulation of Human Motor Cortex," Sheffield University Note published in *The Lancet*, May 11, 1985.

METHOD AND APPARATUS FOR MAGNETICALLY STIMULATING NEURONS

TECHNICAL AREA

This invention is directed to stimulating the neural pathways of an organism and, more particularly, to stimulating the motor and somato sensory neural pathways of higher level organisms, such as the human body.

BACKGROUND OF THE INVENTION

In recent years, methods and apparatus for creating evoked potentials in the neural pathways of higher level organisms (e.g., animals and humans) have been developed. Evoked potentials can produce observable movements and/or analyzable electric signals (e.g., brain waves). Evoked potentials are created by stimulating neural pathways. In the past, three major types of stimulators have been used to create evoked potentials— light, sound and electric stimulators. Light and sound stimulators have been used to stimulate the sensory neural pathways associated with the eyes and ears. Electric stimulators have been used to stimulate motor neural pathways and the sensory neural pathways associated with somatic sensations, i.e., sensations associated with the sense of touch. The present invention is directed to electric stimulation.

In the past, the most common way to electrically stimulate motor and somato sensory neural pathways has been to attach a pair of spaced-apart electrodes to the body at the stimulus location. When electric potential is applied to the electrodes a current flow through the body is created. The current flow produces an electric field that disrupts the polarization of neurons located in the field (commonly called depolarization of the neurons) causing an evoked potential "message" to be transmitted along the neural pathway formed by the depolarized and other neurons that define the neural pathway. When peripheral nerves are being stimulated in this manner, it is usual to attempt supramaximal stimulations so that all neurons are depolarized or "fired" simultaneously. This is done to eliminate variations from stimulus to stimulus and is readily accomplished by applying a current of adequately high magnitude for a sufficient period of time—typically 20–30 milliamperes for 100 microseconds in the case of the human body. In general, the pulse width of a stimulus (50–200 microseconds) is less than the decay time of the neurons to be stimulated (300 microseconds in the case of peripheral neurons). After the stimulus is removed, there may or may not be a reverse recovery current. Even when a recovery current occurs, it is limited to a value that will not itself cause depolarization.

While electric stimulation using a pair of spaced-apart electrodes has certain advantages, it has several disadvantages. One major disadvantage of electrode stimulators relates to the fact that the body is an insulator. As a result, the electric current flow between the electrodes is shallow, i.e., it occurs near the skin. Because current flow is shallow, the electric field created by the current flow is shallow. As a result, deep neurons are not depolarized and, thus, not stimulated. While current can be increased to increase current penetration depth and, thus, stimulation depth, high current flows cause pain and, thus, are undesirable. In fact, pain is one of the major reasons why the use of electrode stimulators to stimulate the brain can only be used on comatose patients. Awake patients generally cannot stand the pain associated with the high current flow needed to stimulate neurons enclosed by cranial bone.

A further disadvantage of electrode stimulators relates to a lack of stimulation selectivity. As noted above, when peripheral neural pathways are stimulated it is usual to attempt supramaximal stimulation. Supramaximal stimulation is used because it stimulates all motor and sensory neural pathways lying in the depolarizing electric field regardless of whether the neural pathways are formed of slow or fast neural fibers. Other stimulation techniques that utilize a spatial relationship are employed to test different speed neural pathways. For example, a collision technique that utilizes two electrode stimulators, one distally (e.g., at the wrist) and the other proximally (e.g., at the elbow), is used to study the slow neural fibers located in the forearm of a patient.

In order to overcome the shallow penetration disadvantage of electrode stimulators, proposals have been made to use a magnetic coil to create a neuron depolarizing electric field. Such devices, commonly called magnetic stimulators, have the advantage of being relatively pain free and noncontacting, as well as capable of stimulating deep and otherwise inaccesible nerves. Depth is improved because, unlike current flow, body tissue does not resist magnetic flux. While magnetic stimulators have the ability to provide deeper penetration with less pain, as best understood, neuron depolarization is still due to the creation of an electric field. More specifically, as best understood, the changing magnetic field created by a magnetic stimulator induces eddy currents in body tissue that, in turn, create a neuron depolarizing electric field.

While magnetic stimulators have certain advantages over electrode stimulators, prior magnetic stimulators have had disadvantages. One major disadvantage of prior methods and apparatus for magnetically stimulating neural pathways is their inefficiency. More specifically, in order to create the large magnetic fields needed to produce a depolarizing electric field in the body of a patient, a large current flow must be created in the coil of the magnetic stimulator. Large current flows are created by rapidly discharging a capacitor bank that has been charged to a high voltage level. Resistance in either or both the capacitor bank charging circuit and the coil discharge circuit produce a loss of energy. Lost energy reduces efficiency. Similarly, creating a capacitor bank charge greater than that needed to produce a depolarizing field results in less than a maximum efficiency system, as does discharging the capacitor bank charge by more than the amount needed to create neuron depolarization. Not only do these techniques create inefficiency, they also unduly prolong charge recovery time and, thus, extend the time between stimulations.

This invention is directed to a method of magnetic stimulation that overcomes the foregoing and other disadvantages and an apparatus for carrying out the method.

SUMMARY OF THE INVENTION

In accordance with this invention, a new and improved method and apparatus for stimulating neural pathways by creating a depolarizing magnetic field is provided. The method of the invention includes creating a sinusoidally fluctuating current flow through a coil that overlies the neurons to be stimulated. The frequency of the current flow and, thus, the frequency of the magnetic field produced by the coil is chosen to correspond in a predetermined manner to the time constant of the neurons to be stimulated. The current and voltage components of the applied power are in phase quadrature with the current lagging the voltage. During the first polarity (e.g., positive) excursion of the applied voltage, the magnetic field produced by the coil is insufficient to produce neuron stimulation, i.e., create a neuron depolarizing electric field. Rather, neuron stimulation occurs during the second polarity (e.g., negative) excursion of the applied voltage. Preferably, coil current flow terminates at the end of the first current cycle. Alternatively, if neuron restimulation during the third, fourth or subsequent polarity excursions of the applied voltage is desired, the coil current can be allowed to decay.

The apparatus of the invention comprises a magnetic stimulator that includes a series circuit (formed by a stimulator coil and large storage capacitor bank) connected in parallel with a power switch across the output of a power supply. Closure of the power switch after the storage capacitors are charged creates a large current flow through the coil. The coil current flow produces a magnetic field that creates a depolarizing electric field that stimulates neurons located in the magnetic field. The resistance of the capacitor discharge circuit, i.e., the coil and the power switch, is maintained low so that capacitor bank recovery current is high. Depending upon the configuration of the power switch, the capacitor discharge can be allowed to ring, i.e. exponentially decay with time, for several current cycles or can be terminated after a single current cycle. Because discharge circuit resistance is maintained low, the circuit is highly under damped whereby the decay rate is low when the capacitor discharge is allowed to ring. Termination at the end of a single cycle is advantageous because it results in a maximum residual charge of the appropriate polarity being retained by the storage capacitors. As a result, the additional charge needed to raise the capacitor voltage to its starting magnitude is minimized.

In accordance with further aspects of this invention, the frequency of the magnetic field produced by the coil, which is controlled by the capacitance of the capacitor bank and the inductance of the coil, is determined by the connection between the coil and the capacitor bank. More specifically, the coil is detachably connected to the capacitor bank. The detachable connection is configured to control the number of capacitors connected in parallel with one another and in series with the coil. The detachable connection controls the frequency of operation of the magnetic stimulator in two ways. First, the detachable connection allows coils of varying inductance to be chosen by a user. Second, the detachable connection allows different capacitor configurations and, thus, different capacitance values to be connected in circuit with the chosen coil. As noted above, control the magnetic stimulator frequency allows the stimulator to be used to selectively stimulate neurons based on the time constant of the neurons. Neurons that have substantially slower or faster time constants than the time constant of the chosen neuron experience less stimulus. In an ideal discharge circuit (no resistance) the period of the magnetic stimulator wave would be set equal to the time constant of the neurons to be stimulated. As a practical matter all circuits have resistance. In a realizable, low resistance discharge circuit the period of the magnetic stimulator wave will fall in the range of 1.25 to 1.43 times the time constant of the neurons to be stimulated.

In accordance with other aspects of this invention, the magnetic stimulator includes an interlock protection circuit that prevents the operation of the stimulator unless a series of predetermined conditions are not met. Preferably, the conditions include: a coil connected to the capacitor bank; coil temperature below a prescribed value; and, the closure of a manually actuable trigger interlock switch.

In accordance with yet other aspects of this invention, the power supply that charges the capacitor bank is a ferro resonant circuit, i.e., a nonlinear resonant circuit that includes a saturable reactor. Because the output current of a ferro resonant power supply is constant from zero until the capacitor bank voltage charge approaches its steady state value, such a power supply is highly efficient and is not destroyed by a shorted output.

In accordance with yet other aspects of this invention, the power switch is triggered by a trigger circuit. Further, preferably, the power switch is formed of solid state components that include a silicon controlled rectifier (SCR) gated on by the trigger circuit and a reverse polarity diode connected in parallel with the SCR. In single cycle embodiments of the invention, the trigger circuit is designed such that the rate of change of voltage at turnoff will not retrigger the SCR. In multiple cycle embodiments of the invention, the trigger circuit is designed such that the rate of change of voltage at turnoff will retrigger the SCR.

This invention also provides a method and apparatus suitable for use in the clinical evaluation of the neurological system of a patient. The method comprises: placing a magnetic stimulator coil on the body of a patient so as to overlie the neurons to be stimulated; applying sinusoidally fluctuating power having voltage and current components in phase quadrature with the current lagging the voltage to said magnetic stimulator coil that causes said magnetic stimulator coil to create a fluctuating magnetic field that stimulates neurons by creating a neuron depolarizing electric field, the frequency of the power applied to the coil and, thus, the frequency of the magnetic field produced by the coil being chosen to correspond in a predetermined manner to the time constant of the neurons to be stimulated, the magnitude of the power being chosen such that neuron stimulation occurs during the second but not the first polarity excursion of the voltage component of the applied power: and, detecting, at a location spaced from the location of said magnetic stimulator coil, evoked potentials created by said stimulated neurons.

In accordance with further aspects of this invention, the clinical method includes the further step of selectively controlling the application of said sinusoidally fluctuating power to said magnetic stimulator coil.

In accordance with other aspects of this invention, the clinical method also includes the steps of: placing electrodes on the body of a patient in the vicinity of said magnetic stimulator coil; and, applying a voltage to said electrodes that causes a current flow between said electrodes that creates a neuron depolarizing electric field.

In accordance with still other aspects of the clinical method of this invention, the neuron depolarizing electric fields created by the magnetic field produced by said magnetic stimulation coil and by current flow between said electrodes are simultaneously produced and combine in an additive manner.

In accordance with yet still other aspects, the invention includes a clinical apparatus that combines a magnetic stimulator formed in accordance with the invention with an evoked potential analyzer and recorder having a trigger output and evoked potential detecting electrodes suitable for connection to the body of a patient at a location remote from the magnetic stimulator coil. The trigger output of the evoked potential analyzer and recorder is connected to the magnetic stimulator power supply for actuating the magnetic stimulator power supply in accordance with a trigger command created by the evoked potential analyzer and recorder.

In accordance with still yet other aspects of this invention, the clinical apparatus includes a pair of stimulator electrodes suitable for positioning on the body of a patient in the vicinity of the magnetic stimulator coil and an electrode power supply for supplying power to said electrodes, the power supply being connected to the trigger output of the evoked potential analyzer and recorder so as to be triggered and apply power to said electrodes when a trigger command is created by said evoked potential analyzer and recorder.

As will be readily appreciated from the foregoing summary, the invention provides a new and improved method and apparatus for stimulating neural pathways. The method and apparatus are highly efficient and have the ability to selectively stimulate neural pathways. Improved efficiency is attributable to several factors, including stimulation on the second polarity excursion of the voltage component of the applied power, retaining of a residual capacitor charge by terminating stimulation at the end of a single cycle and low resistance charge and discharge circuits. Not only are the method and apparatus neurons selective and highly efficient, particularly when operating in a single cycle mode, the method and apparatus have short cycle delay intervals. As a result, the invention is ideally suited for use in clinical environments, as well as laboratory research environments.

BRIEF DESCRIPTION OF THE DRAWINGS

The foregoing and other features and advantages of this invention will become better understood by reference to the following detailed description when taken in conjunction with the accompanying drawings, wherein.

Description of the Preferred Embodiment

Figure 1A:
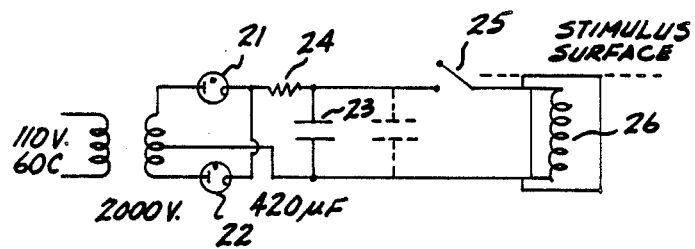
FIGS. 1A and 1B are schematic diagrams of prior art magnetic stimulator circuits.

In order to best understand the major features and advantages of the present invention, it is necessary to first understand the status of existing magnetic stimulator methods and apparatus. An article published in the *Digest of the 6th International Conference on Medical Electronics and Biological Engineering*, 1965, Tokyo entitled "Neuronal Stimulation by Pulsed Magnetic Fields in Animals and Man" by Reginald G. Bickford and Benjamin D. Fremming describes one of the earliest, if not the earliest, magnetic stimulator designed to be used on the human body. FIG. 1A is a reproduction of the circuit disclosed in the paper presented at the conference on which the article is based. As shown in FIG. 1A, a pair of diodes 21 and 22 charge a capacitor 23 via a resistor 24. When a switch 25 is closed the capacitor is discharged through a stimulator coil 26. The result is a rapidly decaying sinusoidal magnetic field that stimulates neurons lying in the field. Since the frequency (500 cps) of the magnetic field is low, the period of the sinusoidal current that produces the magnetic field is relatively long—2 msec. This period is considerably higher than the time constant of motor and sensory neurons. As best understood it has no known correspondence to the time constant of the neurons lying in the stimulating magnetic field. In addition to being inefficient for failing to choose a frequency having a period correspondence of the type described below to the time constant of the neurons to be stimulated, this circuit is inefficient because the capacitor charge decays to zero after each stimulus field is created and because of charging circuit resistor losses. Resistor losses occur during capacitor discharge as well as capacitor charge due to the high reverse voltage that is present on the capacitor during discharge.

Figure 1B:
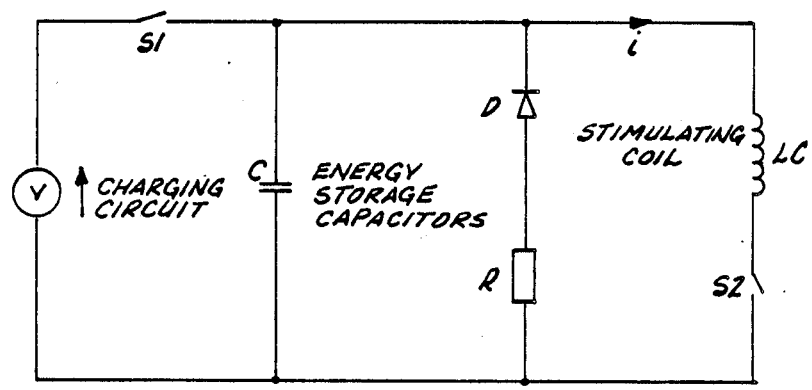

Another example of an existing magnetic stimulator is described in the proceedings of the *IEE International Conference of Electric and Magnetic Fields in Medicine and Biology*, Dec. 1985, pp. 59-63, entitled "The Design, Construction and Performance of a Magnetic Nerve Stimulator" by R. Jalinous, A. T. Barker and I. L. Freeston. The magnetic stimulator circuit disclosed in this paper is illustrated in FIG. 1B. In general, it has many of the same inefficiency disadvantages as the magnetic stimulator circuit illustrated in FIG. 1A. More specifically, the magnetic stimulator circuit illustrated in FIG. 1A comprises a charging circuit V connected to energy storage capacitors C via a first switch S1. A discharge circuit, comprising a stimulator coil $L_c$ connected in series with a second switch S2, is connected in parallel with the energy storage capacitors C. A further series circuit, comprising a diode D connected in series with a resistor R, is also connected in parallel with the energy storage capacitors C. The diode-resistor series circuit is included to protect the energy storage capacitors by limiting the reverse voltage across the energy storage capacitors. While the energy storage capacitors are protected, the diode-resistor series circuit limits the circuit to, in essence, the production of a single stimulus pulse swing; and, makes the stimulator circuit highly inefficient.

Figure 2:
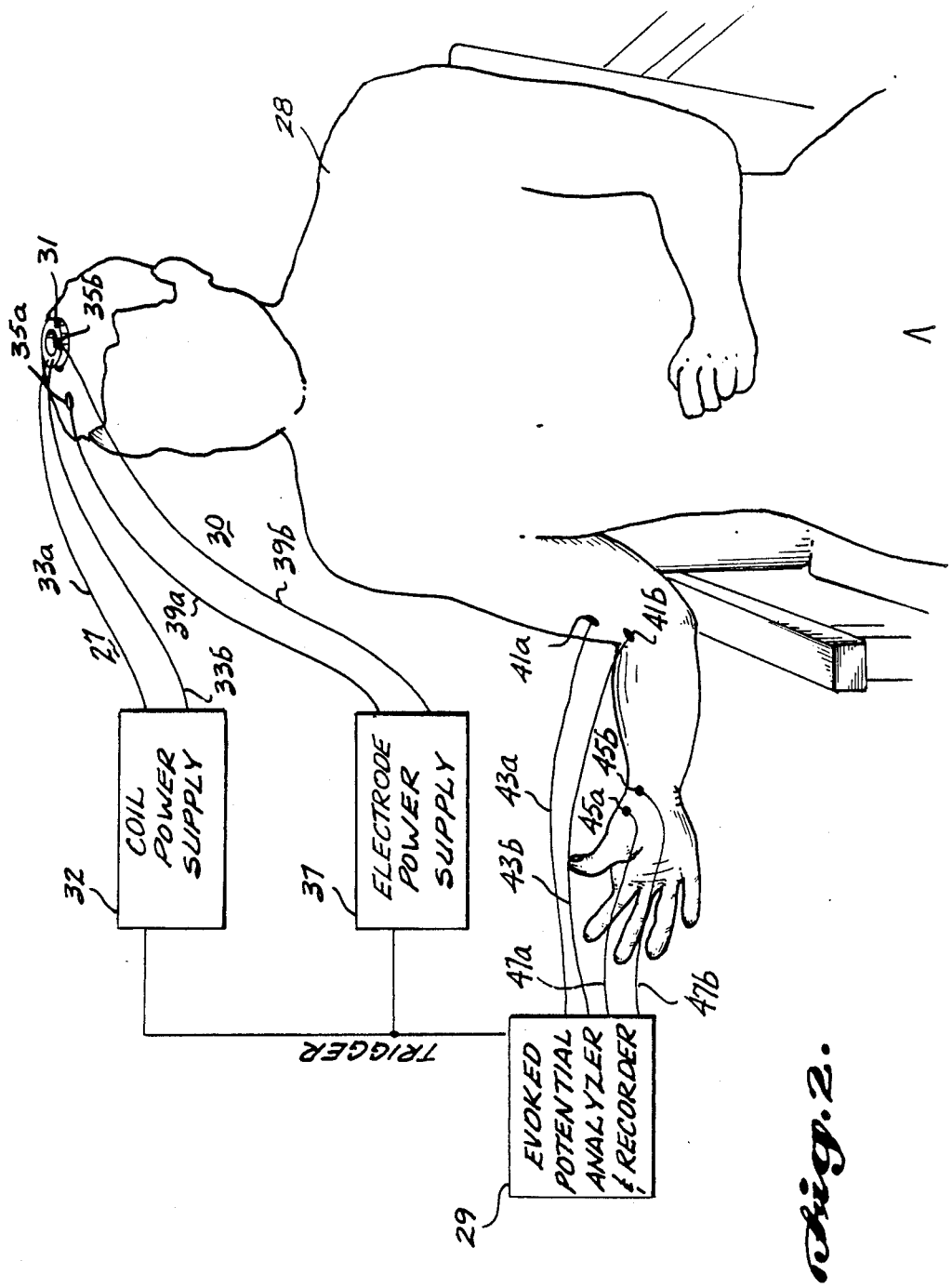
FIG. 2 is a pictorial diagram illustrating a clinical apparatus formed in accordance with the invention for stimulating the cranial neurons of a patient and detecting the evoked potentials occurring in peripheral regions (e.g., the right arm and hand) as a result of such stimulation.

FIG. 2 is a pictorial diagram illustrating an evoked potential diagnostic system that includes a magnetic stimulator 27 formed in accordance with the present invention connected to the body of a patient 28. More specifically, the diagnostic system illustrated in FIG. 1 includes an evoked potential analyzer and recorder 29 and an electrode stimulator 30 as well as the magnetic stimulator 27. The magnetic stimulator 27 includes a stimulator coil 31 and a coil power supply 32 connected to the coil by a pair of wires 33a and 33b. The coil is wound of high current carrying capacity foil—0.010 inch ×0.437 inch copper foil, for example. The electrode stimulator 30 includes a pair of stimulation electrodes 35a and 35b and an electrode power supply 37 connected to the stimulation electrodes by a pair of wires 39a and 39b.

The stimulator coil 31 and the stimulation electrodes 35a and 35b are all positioned atop the cranium of the patient 28. While various orientations can be used, preferably, the coil 31 surrounds one of the stimulation electrodes 35b, and the other stimulation electrode is located beyond the periphery of the coil 31.

The evoked potential analyzer and recorder 29 includes a trigger output that is connected to trigger inputs of the coil power supply 32 and the electrode power supply 37. The evoked potential analyzer and recorder 29 is also connected to a plurality of evoked potential detection electrodes, shown illustratively as two spaced-apart pairs of electrodes. The first pair of evoked potential detection electrodes 41a and 41b are located on the inner surface of the right upper arm of the patient 28, just above the elbow. The first pair of evoked potential detection electrodes are connected to the evoked potential analyzer and recorder 29 by a pair of wires 43a and 43b. The second pair of evoked potential detection electrodes 45a and 45b are located on the inside of the palm of the right hand of the patient just below the thumb and are connected by a pair of wires 47a and 47b to the analyzer and recorder 29. Thus, the pairs of spaced-apart evoked potential detection electrodes 41a and 41b and 45a and 45b span the forearm of the patient 28.

The evoked potential diagnostic system illustrated in FIG. 2 can be operated in a variety of ways. Specifically, when the evoked potential analyzer and recorder 29 is commanded, either manually or automatically, by a diagnostic program ot produce a TRIGGER signal, either one or both of the electrode power supplies can be actuated to apply power to their associated stimulation devices—the stimulator coil 31 and the stimulation electrodes 35a and 35b. That is, a TRIGGER signal can cause the coil power supply 32 to apply power to the coil 31 and the electrode power supply 37 not to apply power to the electrodes 35a and 35b, or vice versa. Alternatively, both the coil power supply 32 and the electrode power supply 37 can be actuated to supply power to both the coil 31 and to the electrodes 35a and 35b, simultaneously or in a predetermined sequence.

Figure 5:
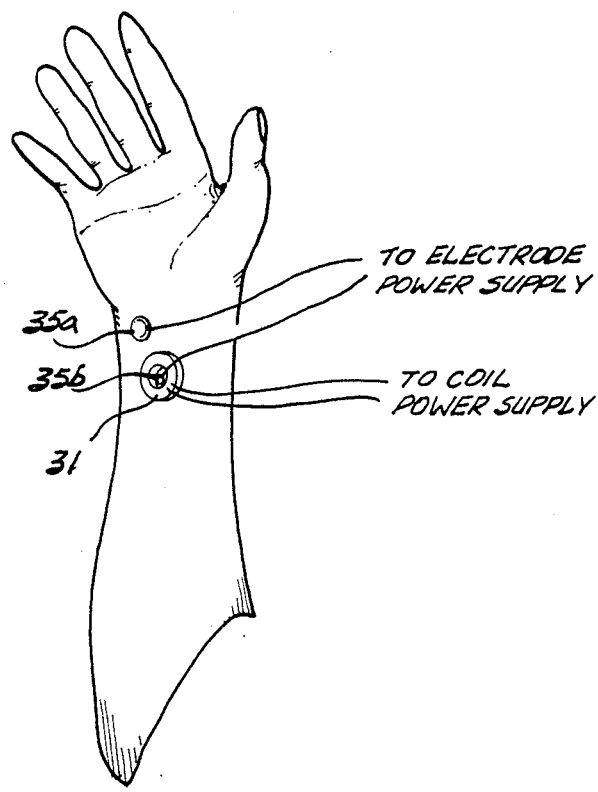
FIG. 5 is an exemplary pictorial diagram illustrating the positioning of stimulator electrodes and a magnetic stimulator coil in the wrist area of a patient.

When an adequate magnitude of power is applied to either the stimulator coil 31 and/or the stimulation electrodes 35a and 35b and the actuated device(s) is correctly positioned on the cranium of the patient 28, an evoked potential is created that can be detected at the evoked potential detection electrodes 41a and 41b and 45a and 45b. The evoked potentials detected at either or both locations are analyzed and/or recorded by the evoked potential analyzer and recorder 29. Since specific analysis and recording techniques do not form part of the present invention, such techniques are not described here. It is to be understood, of course, that the detecting electrodes 41a and 41b and 45a and 45b can be located in a variety of body regions other than those illustrated in FIG. 2. It is also to be understood that the stimulator coil 31 and the stimulation electrodes 35a and 35b can be located in a variety of body regions other than atop the cranium. One such other location is illustrated in FIG. 5 and described below. In summary, it is to be understood that the depicted stimulation and detection locations are to be considered as illustrative, not limiting.

Figure 3:
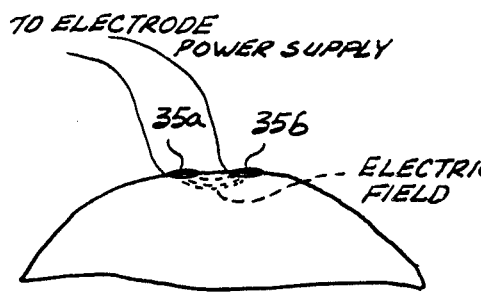
FIG. 3 is a pictorial diagram illustrating a type of electric field created by an electrode stimulator.

FIG. 3 illustrates the type of depolarizing electric field produced in the body of a patient when power is applied to stimulation electrodes 35a and 35b positioned atop the cranium of the patient as illustrated in FIG. 2. As shown in FIG. 3, the electric field created when power is applied to the electrodes is rather shallow. The neuron depolarizing electric field is rather shallow because the current flow between the electrodes (which creates the electric field) is shallow. Because the field is shallow only neurons located near the surface of the cranium are depolarized. While increased power will increase the depth of current flow and, thus, the depth of the electric field, increasing power causes pain and, thus, is unacceptable, except in the case of comatose patients.

Figure 4:
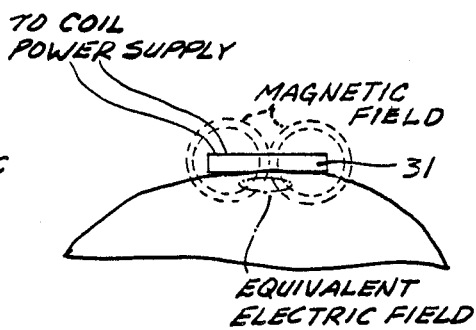
FIG. 4 is a pictorial diagram illustrating the magnetic and electric fields produced by a magnetic stimulator.

FIG. 4 illustrates the type of electric field created when the coil power supply 32 applies power to a stimulator coil 31 positioned atop the cranuim of a patient as illustrated in FIG. 2. As shown in FIG. 4, when energized, the coil 31 creates a magnetic field. The magnetic field in turn sets up eddy currents that create an equivalent electric field. As illustrated in FIG. 4, the electric field created by the coil 31 is considerably deeper than the electric field created by current flow between the stimulation electrodes shown in FIG. 3. While the FIG. 4 electric field is considerably deeper than the FIG. 3 electric field, the pain associated with the creation of an electric field utilizing a magnetic stimulator is substantially less than the pain associated with the creation of an electric field using an electrode stimulator. The pain is less because while the body is an electric insulator it is not a magnetic insulator.

As noted above, FIG. 5 depicts an alternative location for the stimulator coil 31 and the stimulation electrodes 35a and 35b. In FIG. 5 one of the stimulation electrodes 35a is illustrated as positioned on the inside of the wrist of a patient and the other stimulation electrode is located on the end of the underside of the forearm slightly upwardly from the wrist. The stimulator coil 31 encircles the second stimulation electrode 35b. When the stimulation electrodes 35a and 35b and the stimulator coil 31 are positioned in the manner illustrated in FIG. 4, the electric fields produced when the coil power supply 32 and the electrode power supply 37 are simultaneously energized combine to depolarize the underlying neurons. While one or the other of the stimulator coil 31 and the stimulation electrodes could be used separately, this arrangement has the benefit of combining the better focusability of an electrode stimulator with the better depth penetration of a magnetic stimulator.

Figure 6:
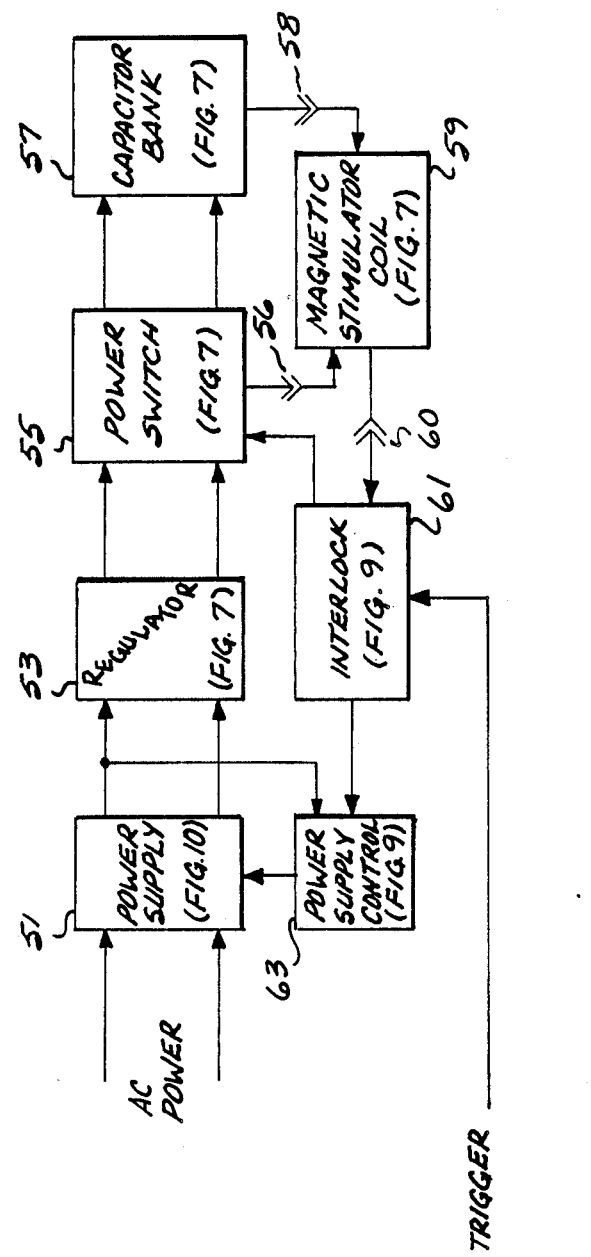
FIG. 6 is a block diagram of a magnetic stimulator formed in accordance with the invention.

FIG. 6 is a block diagram of a magnetic stimulator formed in accordance with the invention. The magnetic stimulator illustrated in FIG. 6 comprises: power supply 51; regulator 53; power switch 55; capacitor bank 57; magnetic stimulator coil 59; interlock 61; and, power supply control 63 circuits. AC line power is applied to the power supply 51, which rectifies the AC power and creates pulsating DC power. The pulsating DC power is applied to the regulator 53. The regulated DC power is applied to a parallel network having one branch formed of the power switch 55 and a second branch formed by the capacitor bank 57 and the magnetic stimulator coil 59. As illustrated, the magnetic stimulator coil 59 is connected to the capacitor bank 57 and the power switch 55 by connectors 56 and 58. Preferably, the connectors form part of a common connector block.

As a result of the foregoing arrangement, when the power switch circuit is open, regulated DC is applied to the capacitor bank 57 resulting in the capacitor bank being charged. When the switch element is closed, the capacitor bank is discharged through the magnetic stimulator coil 59. As a result, the magnetic stimulator coil 59 creates a magnetic field that produces a neuron depolarizing electric field.

Associated with the magnetic stimulator coil 59 are sensors for sensing one or more coil conditions, such as the temperature of the coil, whether the magnetic stimulator coil is connected to the power switch 55 and the capacitor bank 57, etc. The sensed conditions are detected by the interlock circuit 61, which is connected to the magnetic stimulator coil sensors by one or more connectors 60 that, preferably, form part of the common connector block that includes the connectors 56 and 58 that connect the magnetic stimulator coil 59 to the power switch 55 and the capacitor bank 57. The interlock circuit 61 also receives the TRIGGER signal produced by an external device, such as a simple switch or a more sophisticated device such as the evoked potential analyzer and recorder 29 illustrated in FIG. 2 and described above. The interlock circuit produces one or more control signals that are applied to the power supply control circuit 63. The interlock circuit also applies a TRIGGER command to the power switch 55 when the interlock conditions are met and a TRIGGER signal is produced by the external device. The power supply control circuit 63 controls the flow of power from the power supply 51 to the regulator 53. In general, the power supply control circuit 63 controls the power supply such that charge current flows to the capacitor bank via the regulator when the power switch is open and charge current does not flow when the power switch is closed.

Figure 7:
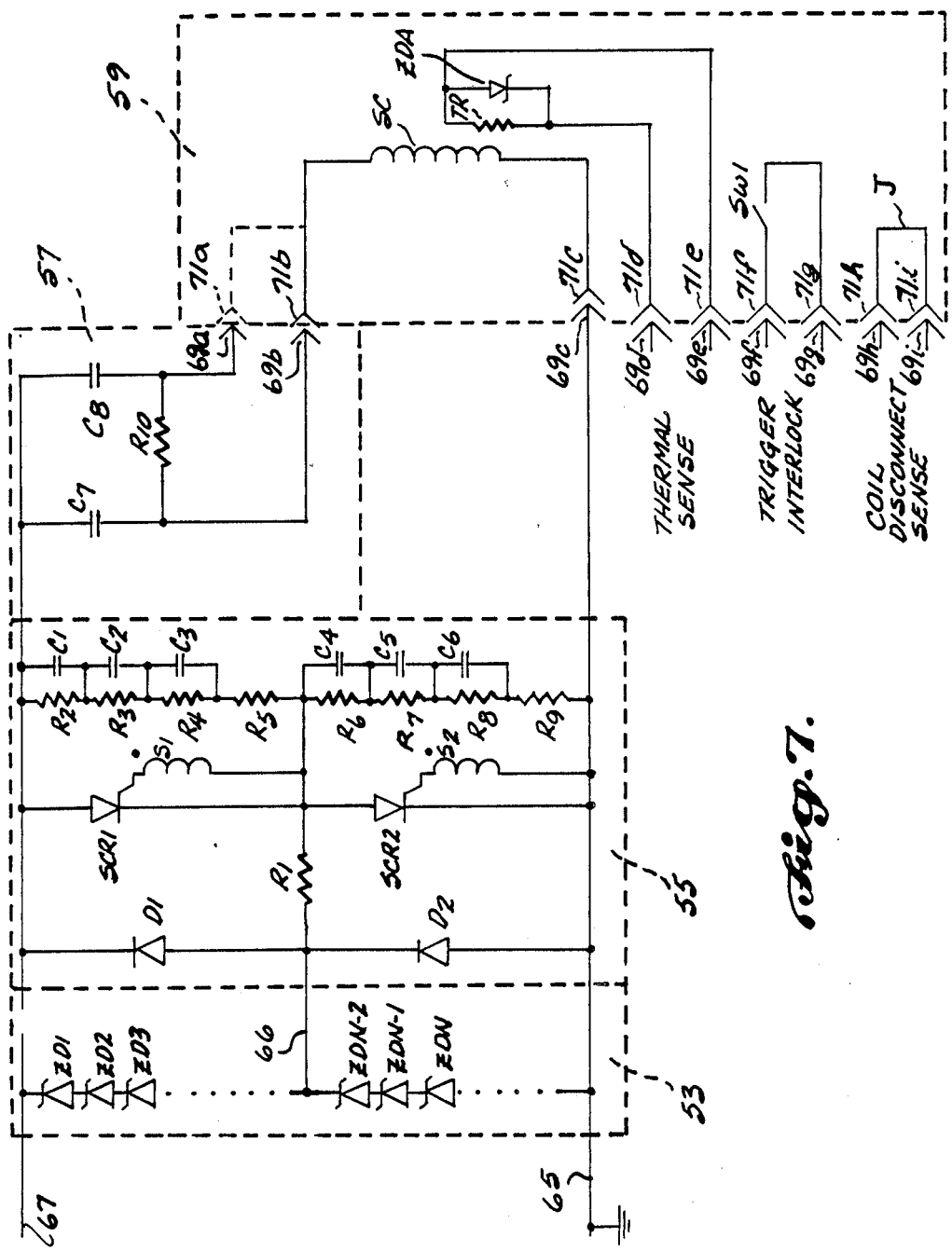
FIG. 7 is a schematic diagram of regulator, power switch, capacitor bank and magnetic stimulator coil circuits suitable for use in the magnetic stimulator illustrated in FIG. 6.
Figure 9:
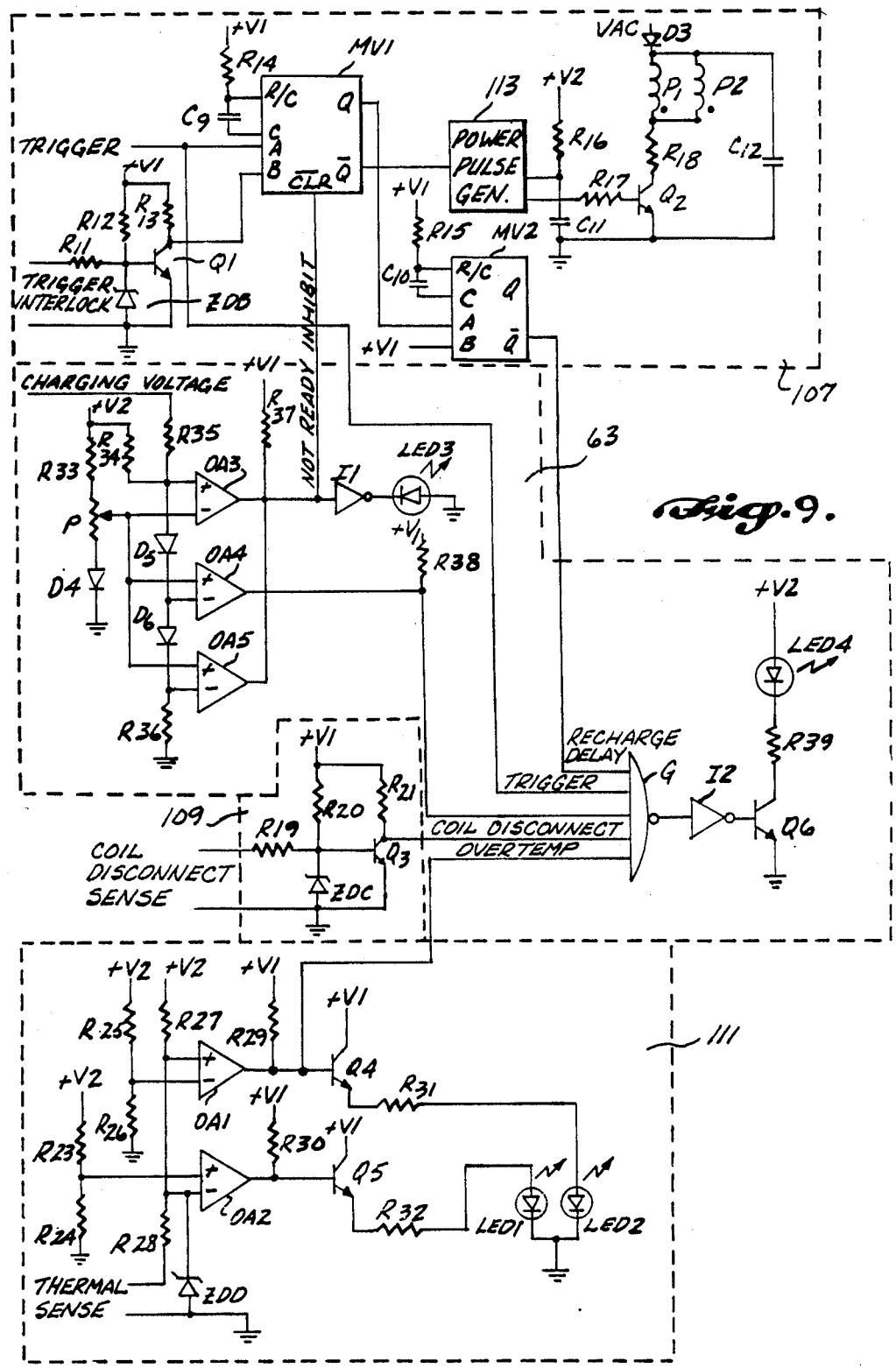
FIG. 9 is a schematic diagram of interlock and power supply control circuits suitable for use in the magnetic stimulator illustrated in FIG. 6.
Figure 8:
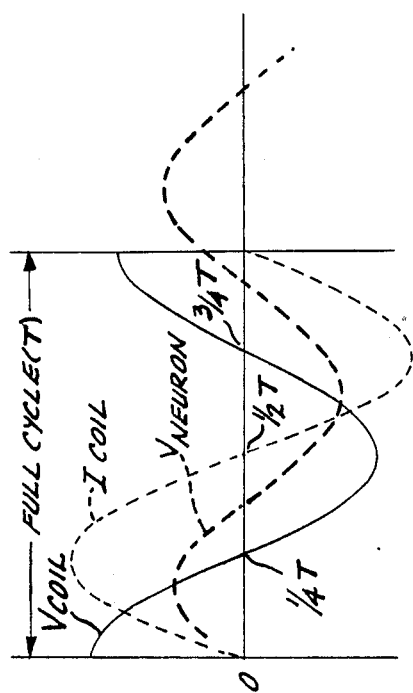
FIG. 8 is a waveform diagram that illlustrates certain aspects of the operation of the power switch, capacitor bank and magnetic stimulator coil illustrated in FIG. 7.

As will be better understood from the following description of the presently preferred circuits illustrated in FIGS. 7-9 for carrying out the functions of the blocks illustrated in FIG. 6, a magnetic stimulator formed in accordance with the invention is highly efficient. Because a switch, rather than a capacitor, is connected across the output of the charging circuit, the reverse polarity voltage applied to the charging circuit when the capacitor is discharged is relatively low. Because reverse polarity voltage is relatively low, the need for a protective resistor in the power supply output is eliminated. Hence, the power loss associated with such a resistor is avoided. Further, because the magnetic stimulator coil 59 is detachably connected to the power switch 55 and the capacitor bank 57, the coil inductance and the capacitor bank capacitance can be tailored to the time constant of the neurons to be stimulated. As will be better understood from the following discussion, such tailoring increases efficiency by focusing on the neurons to be stimulated rather than focusing on stimulating all underlying neruons. Efficiency is further improved by terminating the closure of the power switch such that a residual charge of appropriate polarity remains on the capacitor bank. The retention of a residual charge reduces the amount of charge needed to return the capacitor bank to its starting magnitude after the capacitor bank is discharged to create a neuron depolarizing electric field. As will be better understood form the following description, efficiency is also improved by only charging the capacitor bank to a level that creates neuron depolarization during the second polarity excursion of the discharge voltage swing rather than the first polarity excursion.

FIG. 7 illustrates a voltage reference 53, a power switch 55, a capacitor bank 57 and a magnetic stimulator coil 59 circuit suitable for use in the magnetic stimulator illustrated in FIG. 6. The voltage reference 53 comprises a plurality of zener diodes designated ZD1, ZD2, ... ZDN connected in series across the output of the power supply 51. ZD1, ZD2, ... ZDN are polarized to limit the voltage between the midpoint 66 of the voltage reference and the ground and positive outputs 65 and 67 of the power supply 51 to a predetermined value—1500 volts, for example. The number of zener diodes required by a specific embodiment of the invention will, of course, depend upon the magnitude of the charge voltage produced by the power supply 51 and, the regulating value of the chosen zener diodes.

The power switch 55 comprises a pair of diodes designated D1 and D2; a pair of silicon controlled rectifiers designated SCR1 and SCR2; nine resistors designated R1 through R9; six capacitors designated C1 through C6; and, the secondary windings of a pair of trigger transformers designated S1 and S2. The primary windings of the trigger transformers form a portion of the interlock circuit 61 and are described below. The cathode of D1 is connected to the positive output of the regulator 53 and the anode of D1 is connected to the cathode of D2. The anode of D2 is connected to ground. The junction between D1 and D2 is connected to the center point of the series of zener diodes ZD1-ZDN of the regulator 53. The anode of SCR1 is connected to the positive output of the regulator 53 and the cathode of SCR1 is connected to the anode of SCR2. The cathode of SCR2 is connected to ground. R1 is connected between the junction between D1 and D2 and the junctin between SCR1 and SCR2. R2, R3, R4 and R5 are connected in series in that order between the anode and cathode terminals of SCR1. C1 is connected in parallel with R2; C2 is connected in parallel with R3; and, C3 is connected in parallel with R4. R6, R7, R8 and R9 are connected in series in that order between the anode of SCR2 and the cathode of SCR2. C4 is connected in parallel with R6; C5 is connected in parallel with R7; and, C6 is connected in parallel with R8. S1 is connected between the gate of SCR1 and the cathode of SCR1; and, S2 is connected between the gate of SCR2 and the cathode of SCR2.

As will be readily appreciated by those skilled in the art and others from the foregoing description and viewing the power switch illustrated in FIG. 7, when the switch elements—SCR1 and SCR2—are gated off, no current flows through the SCR1 and SCR2 or their related antipolarized diodes D1 and D2. When SCR1 and SCR2 are triggered by a suitable voltage at the terminals of S1 and S2, respectively, current flows through SCR1 and SCR2. If the voltage across SCR1 and SCR2 is sinusoidal, current flows through SCR1 and SCR2 as long as a gate voltage of suitable polarity is present on the gates of SCR1 and SCR2, and the anodes of SCR1 and SCR2 are positive with respect to their cathodes. When the polarity of the voltage across SCR1 and SCR2 reverses, current flow through SCR1 and SCR2 ends regardless of the presence of a voltage on the gates of SCR1 and SCR2. During voltage reversals, current flows through the antipolarized diodes D1 and D2. The circuits formed by R2-R5 and C1-C3 and R6-R9 and C4-C6 are snubber circuits. More specifically, these circuits prevent SCR1 and SCR2 from being retriggered after being triggered (in the absence of a trigger voltage on the output of S1 and S2, respectively) by limiting the rate of voltage change at SCR turnoff to below that required for retriggering.

The capacitor bank 57 illustrated in FIG. 7 comprises: a pair of high voltage, large storage capacitors designated C7 and C8; and, a resistor designated R10. The ends of C7 and C8 are connected together and to the positive voltage side of the power switch circuit 55. R10 is connected across the other ends of C7 and C8. The junction between R10 and C8 is aslo connected to one terminal 69a of a male connector block and the junction between C7 and R10 is connected to another terminal 69b of the male connector block. The ground side of the power switch is connected to a further terminal 69c of the male connector block.

As noted above, the magnetic stimulator coil 59 is a circuit that includes a number of condition sensors in addition to a stimulator coil, which is designated SC in FIG. 7. The condition sensors include: a temperature sensing circuit that comprises a temperature sensing resistor designated TR and, a zener diode designated ZDA; a trigger interlock sensor comprising a single pole, single throw switch designated SW1; and, a coil disconnect sensor comprising a jumper designated J. TR is positioned in the vicinity of SC to sense the temperature of SC.

One end of SC is connected to one or more terminals 71a and 71b of a female connector block designed to mate with the male connector block. The chosen terminals correspond to the terminals 69a and 69b connected to the storage capacitors C7 and C8 of the capacitor bank circuit 57. The other side of SC is connected to another (third) terminal 71c of the female terminal block. The chosen terminal is the one that corresponds to the terminal 69c of the male connector block connected to the ground side of the power switch.

One end of TR and the cathode of ZDA are connected to a fourth terminal 71d of the female terminal block. The other end of TR and the anode of ZDA are connected to a fifth terminal 71e of the female terminal block. SW1 is connected across the sixth and seventh terminals 71f and 71g of the female terminal block; and, J is connected across the eighth and ninth teminals 71h and 71i. The terminals 69d and 69e of the male terminal block that mate with the fourth and fifth terminals 71d and 71e of the female terminal block are connected to a thermal sense circuit that forms part of the hereinafter described interlock circuit. The terminals 69f and 69g of the male terminal block that mate with the sixth and seventh terminals 71f and 71g of the female terminal block are connected to a trigger interlock circuit that aslo forms part of the hereinafter described interlock circuit illustrated in FIG. 8. Finally, the terminals 69h and 69i of the male terminal block that mate with the eighth and ninth terminals 71h and 71i of the female terminal block are connected to a coil disconnect sense circuit that forms a further part of the hereinafter described interlock circuit.

As noted above, in the absence of a gate voltage across the terminals of S1 and S2, SCR1 and SCR2 are open. When SCR1 and SCR2 are open the power switch draws substantially zero current. As a result, as far as the power supply is concerned, the power switch doesn't exist when the capacitor bank is being charged. Thus, all of the power produced by the power supply is used to charge C7 and/or C8. In this regard, it is to be understood that C7 and C8 are representative of a capacitor bank. If desired, any number of additional capacitors, connected in a similar manner, and a corresponding number of male and female terminals can be included in the capacitor bank of an actual embodiment of the invention. Whichever capacitors are connected via the male and female terminal blocks to SC are charged by the power supply. During charging, the current flow through SC is relatively low.

When an SCR trigger voltage is created across the terminals of S1 and S2, SCR1 and SCR2 are both gated on. As a result, the output of the power supply is shorted, resulting in the charge stored in the charged capacitors (C7 and/or C8) being applied to the stimulator coil, SC. Because the discharge circuit is highly under damped due to the resistance of the tank circuit formed by SCR1, SCR2, SC and C7 (and/or C8) being very low, a high current flows through SC, resulting in SC generating a large magnetic field. The frequency of the tank circuit is dependent upon the inductance of SC and the capacitance of the charged capacitors. The connector block allows this frequency to be controlled by controlling these inductance and capacitance values. Inductance is controlled by choosing a magnetic stimulator coil SC having a desired inductance value. Capacitance is controlled by configuring the female connector such that the number of capacitors connected to the capacitor bank terminals of the connector block create the desired capacitance value. As will be better understood from the following discussion, the inductance and capacitance values are chosen such that the period of the field produced by SC, which is determined by the period of the current flow through SC corresponds in a chosen way to the time constant of the neurons to be depolarized.

As noted above, the circuits formed by R2-R5 and C1-C3; and, R6-R9 and C4-C6 form snubber circuits that prevent the retriggering of SCR1 and SCR2 unless or until gating voltages are again applied to SCR1 and SCR2 by S1 and S2. As a result, each time SCR1 and SCR2 are gated closed a single discharge cycle occurs. During the first half of the cycle current flows through SCR1 and SCR2, during the second half of the cycle current flows through reverse polarity diodes D1 and D2. This mode of operation is depicted in FIG. 8. More specifically, as shown in FIG. 8, the coil current ($I_{coil}$) and voltage ($V_{coil}$) are in phase quadrature with the current lagging the voltage. Starting at when SCR1 and SCR2 are gated closed, $V_{coil}$ is a cosine function and $I_{coil}$ is a sine function. Hence, the coil voltage starts at a large value (e.g., 3000 volts) in a first polarity direction (e.g., positive) and sinusoidally drops to zero during the first quarter of the first sinusoid (between 0 and $\frac{1}{4}T$, where T represents the period of the sinusoid). During the second and third quarters of the first sinusoid (between $\frac{1}{4}T$ and $\frac{3}{4}T$), the voltage swings in the other polarity direction (e.g., negative) before returning to zero. During the fourth quarter of the first sinusoid, the voltage again swings positive, reaching a value slightly less than the starting voltage value. The magnitude of the reduction is, of course, dependent upon circuit resistance. During the first or second quarters of the current sinusoid ($0-\frac{1}{2}T$), the current swing is in the same polarity direction as the fiest voltage swing (e.g., positive). During this part of the current sinusoid, current flows through SCR1 and SCR2. During the third and fourth quarters of the current sinusoid ($\frac{1}{2}$ T to T), the current swing is in the other polarity direction (e.g., negative), whereby current flows through D1 and D2. Since SCR1 and SCR2 are gated off prior to the end of the current sinusoid, current flow through the coil terminates at the end of the current sinusoid.

As will be readily appreciated from viewing FIG. 8 and the foregoing description, the recovery current creates a residual voltage on C7 (and/or C8) at the end of the single cycle of operation. As shown in FIG. 8, the magnitude of the residual voltage is substantially the same as the magnitude of the voltage present on C7 (and/or C8) at the beginning of the single cycle of operation. As a result, very little additional charge needs to be added in order to return the C7 (and/or C8) charge to its starting level and, thus, be ready for a second cycle of operation. While, as described below, a magnetic stimulator formed in accordance with the invention can be configured to operate in a multiple cycle manner, there are advantages to a single cycle mode of operation. These advantages include the efficiency and short between cycle times resulting from the high residual storage capacitor charge.

The positioning of the power switch circuit 55 across the output of the regulator circuit 53 leads to further efficiency regardless of whether SCR1 and SCR2 are gated on for a single or multiple cycles of operation. In this regard, when SCR1 and SCR2 are closed, the voltage across the switch is relatively low. Consequently, the voltage across the output of the power supply circuit 51 in the reverse direction, i.e., when current flows through D1 and D2, is relatively low. Because the reverse voltage across the power supply circuit 51 is relatively low, there is no need to include protective resistors in the output of the power supply circuit 51. Because the need for protective resistors is avoided, losses associated with such resistors are avoided. As a result, the efficiency of a magnetic stimulator formed in accordance with the invention is greater than the efficiency of magnetic stimulators wherein a capacitor is connected across the output of a power supply. In this regard, when the capacitor of a tank circuit is connected across the output of a power supply, relatively large reverse voltages are applied to the power supply. If protective resistors are not connected in the output of the power supply, the high reverse voltage will destroy the diode rectifiers of the power supply. While shorting the output of a power supply will cause a high current drain that can destroy some types of power supplies, as will be better understood from the following description, the power supply chosen by the invention is a constant current (at low voltages) power supply that is not destroyed when its output is shorted.

As noted above and as illustrated in FIG. 9, the interlock circuit 61 actually comprises three separate interlock circuits—a trigger interlock circuit 107; a coil disconnect interlock circuit 109; and, a thermal interlock circuit 111. In addition to functioning as an interlock, the trigger interlock circuit also functions as a trigger circuit. More specifically, the trigger interlock circuit 107 comprises: two monostable multivibrators designated MV1 and MV2; a power pulse generator 113; two NPN transistors designated Q1 and Q2; a zener diode designated ZDB; a diode designated D3; four capacitors C9, C10, C11 and C12; eight resistors designated R11–R18; and, the primary windings of the trigger transformers, which are designated P1 and P2. One of the trigger interlock terminals, namely the sixth terminal 69f of the male connector block (FIG. 7), is connected to ground. The other trigger interlock terminal 69g of the male connector block is connected to one end of R11. The other end of R11 is connected to the base of Q1 and to the cathode of ZDB. The anode of ZDB is connected to ground. The emitter of Q1 is also connected to ground. The base of Q1 is also connected through R12 to a first regulated voltage bus designated +V1. The emitter of Q1 is connected through R13 to +V1. The collector of Q1 is also connected to a control (B) input of MV1.

The externally generated TRIGGER signal is applied to the trigger (A) input of MV1. The TRIGGER signal is also applied to one of the inputs of a five input NAND gate, designated G, that forms a part of the hereinafter described power supply control circuit 63. C9 is connected between the R/C and C terminals of MV1. The R/C terminal is also connected through R14 to +V1. The Q output of MV1 is connected to the trigger (A) input of MV2. The control (B) input MV2 is connected to +V1. C10 is connected between the R/C and C terminals of MV2 and the R/C terminal of MV2 is connected through R15 to +V1. The $\overline{Q}$ output of MV2 is connected to a second input of G.

The $\overline{Q}$ output of MV1 is connected to the trigger input of the power pulse generator 113. The pulse period control input of the power pulse generator 113 is connected through R16 to a second regulated voltage bus designated +V2 and through C11 to ground. The pulse output of the power pulse generator is connected through R17 to the base of Q2. The emitter of Q2 is connected to ground. The collector of Q2 is connected through R18 to one end of P1 and P2. The other ends of P1 and P2 are connected to the cathode of D3. The anode of D3 is connected to an AC power bus created by the power supply in the manner illustrated in FIG. 10 and described below. The junction between the cathode of D3 and P1 and P2 is connected through C12 to ground.

As will be readily appreciated by those skilled in the art and others, the values R14 and C9 control the pulse period of MV1; the values of R15 and C10 control the pulse period of MV2 and the values of R16 and C11 control the pulse period of the power pulse generator. By way of example, in one actual embodiment of the invention, the pulse period of MV1 was chosen to be two microseconds; the pulse period of MV2 was chosen to be 15 milliseconds; and, the pulse period of the power pulse generator was chosen to be 10 microsends.

In operation, when the trigger interlock switch (SW1) is closed Q1 is rendered nonconducting and, thus, the voltage on the B input of MV1 is high. This high enables MV1 to respond to a negative going TRIGGER pulse. When SW1 is open, MV1 is disabled, i.e., MV1 cannot respond to a negative going TRIGGER pulse because the B input of MV1 is grounded by Q1. Preferably, SW1 is a manually operated switch located in a handle on which the stimulator coil, SC, is mounted. When constructed in this manner a user can place the coil on the body of a patient and manually enable MV1 when the coil is suitably positioned. Alternatively, SW1 could be located on a console or in some other suitable position.

When MV1 is enabled and responds to a negative going TRIGGER pulse, the Q output of MV1 shifts from a low state to a high state and the $\bar{Q}$ output of MV1 shifts from a high state to a low state. The low/high shift of the Q output of MV1 triggers MV2 resulting in the $\bar{Q}$ output of MV2 shifting from a high state to a low state. As will be better understood from the following description of the power supply control circuit 63, this high/low shift disables G. Prior to this shift the negative going TRIGGER pulse disabled G.

The pulse produced at the $\bar{Q}$ output of MV1 when MV1 is triggered, triggers the power pulse generator 113. The power pulse generator produces a positive pulse for a predetermined period of time, e.g., 10 microseconds, during which Q2 conducts. As a result, half wave rectified AC pulses current flow through P1 and P2. The current flow through P1 and P2 causes current to flow through S1 and S2, resulting in SCR1 and SCR2 being triggered on.

In essence, MV1 and the power pulse generator 113 form a nonretriggerable combination that makes certain that the SCRs will fire fast enough to prevent this destruction. While various multivibrators and power pulse generators can be used with the invention, in one actual embodiment, MV1 and MV2 were LS221 Monostable Multivibrators produced by Texas Instruments, Inc., Dallas, Tex. and the power pulse generator 113 was a Series 555 Pulse Generator produced by National Semiconductor Corp., Santa Clara, Calif.

The coil disconnect interlock circuit 109 comprises a zener diode designated ZDC; three resistors designated R19, R20 and R21; and, an NPN transistor designated Q3. One of the coil disconnect sense terminals, namely the eighth terminal 69h, of the male connector block is connected to one end of R19 and the other coil disconnect sense terminal 69i of the male connector block is connected to ground. The other end of R19 is connected to the cathode of ZDC, the base of Q3 and through R20 to +V1. The anode of ZDC is connected to ground. The emitter of Q3 is connected to ground and the collector of Q3 is connected through R21 to +V1. The collector of Q3 is also connected to a third input of the five input gate, G, that forms part of the power supply control circuit 63. In essence, when the coil disconnect sense end of R19 is ungrounded because the male and female connector blocks are unconnected, the voltage at the base of Q3, which is then controlled by ZDC, turns Q3 on. The resulting low voltage on the collector of Q3 disables G. When the male and female connector blocks are connected, the voltage at the base of Q3 shifts low, whereby Q3 is rendered nonconducting. When Q3 is nonconducting the voltage at the collector of Q3 is high and G is enabled.

The thermal interlock circuit 111 comprises: two operational amplifiers designated OA1 and OA2; a zener diode designated ZDD; two NPN transistors designated Q4 and Q5; two light emitting diodes designated LED1 and LED2; and, ten resistors designated R23-R32. R23 and R24 are connected in series between +V2 and ground. The junction between R23 and R24 is connected to the noninverting input of OA2. R25 and R26 are connected in series between +V2 and ground. The junction between R25 and R26 is connected to the inverting input of OA1. R27 and R28 are connected in series between +V2 and one of the thermal sense terminals, namely the fifth terminal 69e, of the male connector block. The other thermal sense terminal 69d of the male connector block is connected to ground. The junction between R27 and R28 is connected to the noninverting input of OA1 and the inverting input of OA2. The noninverting input of OA1 and the inverting input of OA2 are also connected to the cathode of ZDD. The anode of ZDD is connected to ground. The output of OA1 is connected through R29 to +V1 and the output of OA2 is connected through R30 to +V1. The output of OA1 is also connected to the base of Q4 and the output of OA2 is also connected to the base of Q5. The collectors of Q4 and Q5 are connected to +V1. The emitter of Q4 is connected through R31 to the anode of LED2. The collector of Q5 is connected through R32 to the anode of LED1. The cathodes of LED1 and LED2 are connected to ground. The output of OA1 is also connected to the fourth input of the five input NAND gate, G, that forms part of the power supply control circuit 63.

In operation, when a magnetic stimulator coil and its related sensors are connected to the capacitor bank, the power switch and the interlock circuit, the coil temperature sensing resistor, TR, controls current flow through a series circuit formed by R27, R28 and TR. As a result, the resistance value of TR, which is controlled by temperature, controls the voltage at the noninverting input of OA1 and the inverting input of OA2. This voltage is compared by OA1 with the voltage at junction between R25 and R26 and by OA2 with the voltage at junction between R23 and R24. If the temperature of the coil, as sensed by TR, is below a prescribed level, the output of OA1 is positive, i.e., high. The high output of OA1 enables gate G. The high output of OA1 also causes current to flow through Q4, resulting in LED2 being lit. Contrariwise, when the coil temperature is low, the output of OA2 is low. As a result, Q5 is rendered nonconducting and LED1 is not lit. When the temperature of the coil, SC, exceeds the prescribed level, the voltage at the noninverting input of OA1 and the inverting input of OA2 changes such that the outputs of OA1 and OA2 reverse. As a result, the gate, G, is disabled; LED2 is turned off; and, LED1 is lit. Consequently, the lit/unlit states of LED1 and LED2 denote whether the temperature of the coil is above or below a prescribed level.

In addition to the five input NAND gate, G, the power supply control circuit 63 illustrated in FIG. 9 comprises: three operational amplifiers designated OA3, OA4 and OA5; three diodes designated D4, D5 and D6; seven resistors designated R33-R39; a potentiometer designated P; two inverters designated I1 and I2; a light emitting diode designated LED3; an NPN transistor designated Q6; and, the light emitting diode of an optical coupler designated LED4. +V2 is connected through R33 in series with P to the anode of D4. The cathode of D4 is connected to ground. The output of the power supply 51, i.e., the charging voltage, is applied through R35 to the anode of D5. The cathode of D5 is connected to the anode of D6 and the cathode of D6 is connected through R36 to ground. The junction between R35 and the anode of D5 is connected to the noninverting input of OA3 and through R34 to +V2. The junction between the cathode of D5 and the anode of D6 is connected to the inverting input of OA4. The junction between the cathode of D6 and R36 is connected to the inverting input of OA5. The inverting input of OA3, and the noninverting inputs of OA4 and OA5 are connected to the adjustable terminal of P. The outputs of OA3 and OA5 are connected through R37 to +V1 and to a clear control input of MV1 of the trigger interlock circuit 107. The outputs of OA3 and OA5 are also connected through I1 to the cathode of LED3. The anode of LED3 is connected to ground. The output of OA4 is connected through R38 to +V1 and to the fifth input of G. The output of G is connected through I2 to the base of Q6. The emitter of Q6 is connected to ground. The collector of Q6 is connected through R39 to the cathode of LED4. The anode of LED4 is connected to +V2.

When the four control inputs, namely the two inputs received from the trigger interlock circuit 107 and the inputs received from the coil disconnect interlock circuit and the thermal interlock circuit, of G are high, G is enabled and tracks the output of OA4. When any of the control inputs are high G is disabled, i.e., the output of G remains high regardless of fluctuations in the output of OA4. Thus, when a coil is connected by the male and female connector blocks to the capacitor bank, the power switch and the interlock circuit; the coil temperature is below a predetermined level; no TRIGGER signal is present; and the $\overline{Q}$ output of MV2 is high the output of G is controlled by the output of OA4. Since the output of OA4 is controlled by the setting of P, the setting of P controls the output of OA4 when G is enabled by all of its control inputs. The output of G is inverted by I2 and the output of I2 controls the flow of current through Q6. When G is disabled, the output of G is high, the low output of I2 renders Q6 nonconducting. When G is enabled, the output of OA4 via G and I2 controls the flow of current through Q6 and, thus, the emission of light by LED4 to its associated photo transistor, which forms part of the hereinafter described power supply 51 (FIG. 10).

When a trigger pulse occurs, i.e., the TRIGGER signal shifts from a high state to a low state, G is immediately disabled, i.e., the output of G shifts high, whereby the output of I2 shifts low and Q6 is switched off. Thereafter, during the pulse interval of MV2, the $\overline{Q}$ output of MV2 shifts low maintaining G disabled. At the end of the MV2 pulse period, G becomes enabled and the output of I2 tracks the output of OA4. As a result, the output of OA4 again controls the current flow through Q6 and, thus, the emission of light by LED4. OA4 compares the voltage at the junction of D5 and D6, which represents charge on the storage capacitors of the capacitor bank circuit, with the voltage at the adjustable terminal of P. This voltage difference controls current flow through Q6 and, thus, through LED4.

The outputs of OA3 and OA5 prevent the triggering of MV1 and, thus, the triggering of the power switch unless the capacitor bank charge lies within a predetermined range of the voltage on the adjustable terminal of P. The range is controlled by the voltage drops of D5 and D6. If the capacitor bank voltage lies outside of the chosen range the output of OA3 or the output of OA5, depending upon whether the voltage is above or below the range will cause the NOT READY INHIBIT line to go low and hold MV1 in a clear state. Thus, MV1 is prevented from being triggered by a TRIGGER pulse. The same output, via I1, will cause LED3 to light. In this way, the user will be advised that the capacitor bank charge is at an incorrect (usually low) level and, thus, not ready to create a neuron depolarizing magnetic field.

Figure 10:
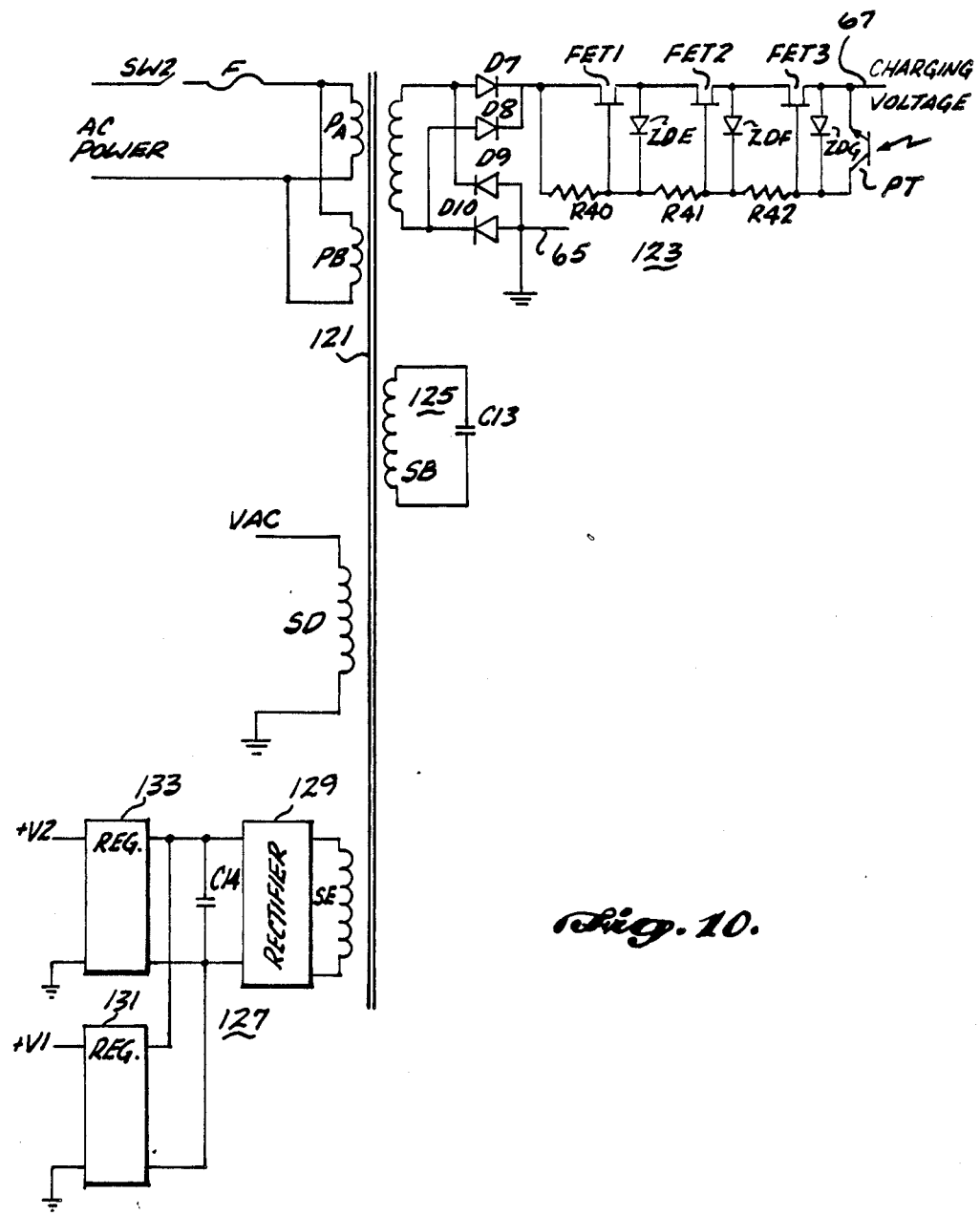
FIG. 10 is a schematic diagram of a power supply circuit suitable for use in the magnetic stimulator illustrated in FIG. 6.

The power supply circuit illustrated in FIG. 10 comprises: a saturable reactor 121; a rectifier section 123; a resonant frequency control section 125; and, a DC subsection 127. AC power is applied through a switch designated SW2 in series with a fuse designated F to the primary windings PA and PB of the saturable reactor 121.

The rectifier section 123 comprises: four high voltage rectifier diodes designated D7, D8, D9 and D10; three field effect power transistors designated FET1, FET2 and FET3; three zener diodes designated ZDE, ZDF and ZDG; three resistors designated R40, R41 and R42; and, the photo transistor portion of the optical coupler associated with LED4 (FIG. 9) designated PT. One end of a secondary winding designated SA of the saturable reactor 121 is connected to the anode of D7 and to the cathode of D9. The other end of the SA is connected to the anode of D8 and to the cathode of D10. The anodes of D9 and D10 are connected to ground and the cathodes of D7 and D8 are connected to the source of FET1. The drain of FET1 is connected to the source of FET2 and the drain of FET2 is connected to the source of FET3. The drain of FET3 is connected to the emitter of PT. The cathodes of D7 and D8 are also connected to one end of R40. The other end of R40 is connected to the gate of FET1, the cathode of ZDE and one end of R41. The other end of R41 is connected to the gate of FET2, the cathode of ZDF and one end of R42. The other end of R42 is connected to the gate of FET3, the cathode of ZDG and the collector of PT. The anode of ZDE is connected to the junction between the drain of FET1 and the source of FET2; the anode of ZDF is connected to the junction between the drain of FET2 and the source of FET3; and, the anode of ZDG is connected to the junction between the drain of FET3 and the emitter of PT. The positive output 67 of the power supply circuit, which is connected to the regulator circuit 53 illustrated in FIG. 7 and described above, occurs at the drain of FET3. Thus, the voltage at the drain of FET3 is the capacitor bank charging voltage.

As will be readily appreciated by those skilled in the art from the foregoing description and viewing FIG. 10, the voltage at the output of the bridge formed by D7, D8, D9 and D10 is a full wave rectified AC voltage. FET1, FET2 and FET3 form the equivalent of a high voltage transistor power switch that controls the flow of charging current based on the receipt of light by PT from LED4. As described above, the emission of light by LED4 is controlled by the difference between the charging voltage, which is the same as the capacitor bank charge, and the setting of P.

The resonant frequency control section 125 of the power supply circuit comprises a capacitor designated C13 connected across SB. The value of the capacitor controls the resonant frequency of the power supply circuit.

As will be readily appreciated from the foregoing description, the power supply circuit is a ferro resonant circuit, i.e., a resonant circuit that includes a saturable reactor that gives the circuit nonlinear characteristics. As will be appreciated by those skilled in the art, a power supply constructed in the manner illustrated in FIG. 10 does not self-destruct when the output is shorted, i.e., when the power supply charging output 67 is connected to ground, as occurs when SCR1 and SCR2 are gated on and current flows to SCR1, SCR2, D1 and D2 during alternate portions of the capacitor bank discharge cycle. A ferro resonant circuit of the type illustrated in FIG. 10 has the further advantages of being more efficient than a standard transformer power supply circuit; and, not creating an excessive output voltage.

The saturable reactor 121 includes a third secondary winding (which is actually on the primary side of the reactor) designated SD. One side of SD is connected to ground and the second side connected to the AC input of the trigger interlock circuit 107 (FIG. 9). Thus, this winding supplies AC power to the primary windings, P1 and P2, of the trigger transformers.

The DC section 127 comprises a rectifier 129, which may be formed by four diodes connected similar to D7–D10 or D11–D14; a capacitor designated C14; and, two regulators 131 and 133.

The saturable reactor 121 has a fourth secondary winding (which is also on the primary side of the reactor) designated SE. SE is connected to the input of the rectifier 129; and, C14 is connected across the outputs of rectifier 129. The outputs of the rectifier 129 are also connected to the inputs of the regulators 131 and 133. +V1 is formed at the output of the first regulator 131 and +V2 is formed at the output of the second regulator 133.

As will be readily appreciated from the foregoing description, a magnetic stimulator formed in accordance with the invention is highly efficient. Improved efficiency results from the fact that the resistance of the storage capacitor charge and discharge circuits is minimized. Thus, energy losses associated with these high current flow circuits are avoided. Even though relatively high instantaneous voltages and currents (3,000 volts and 9,000 amps) occur in actual embodiments of the invention, danger is minimized by an interlock protection circuit that prevents the inadvertent generations of these high voltages and currents.

As illustrated in FIG. 8, the neuron depolarization voltage created when the magnetic stimulus coil is suitably positioned on the body as exemplary illustrated in FIGS. 2 and 5, is greater in magnitude during the second and third quarters of the cycle of operation than during the first quarter. In accordance with this invention, this phenomena is utilized to achieve even greater efficiency. More specifically, rather than attempting to obtain depolarization during the first one quarter of the cycle of operation, as in prior art magnetic stimulators, the storage capacitor charge is held below the level necessary to depolarize neurons during the first quarter cycle of operation, but above the level necessary to depolarize during the second and third quarters of the cycle of operation. This decrease in the required starting charge increases overall efficiency. In addition to choosing voltage levels that meet the just discussed criteria, the invention also contemplates selecting the capacitance of the capacitor bank and the inductance of the magnetic stimulator coil such that the discharge cycle time (i.e., the cycle period T shown in FIG. 8) corresponds to the time constant of the neurons to be stimulated. In this regard, neuron stimulation time constants generally fall in the range from 50–300 microseconds, the time constant of brain neurons being located at the lower end of this range and the time constant of peripheral neurons being located toward the upper end of this range.

In the ideal situation, i.e., no resistance in the capacitor discharge circuit, the capacitance and inductance values would be chosen such that the period T would equal the time constant of the neurons to be stimulated. Because a zero resistance discharge circuit cannot be created, the ideal result cannot be realized. While the ideal case cannot be realized, the judicious selection of components can result in the creation of a minimum resistance discharge circuit. When this is done, discharge circuit resistance in the 30–50 milliohm is achievable. Such a practical, realizable discharge circuit produces maximum stimulation when the period of the magnetic field and, thus, the period of the current through SC falls in the range of 1.25–1.43 times the time constant of the neurons to be stimulated. Periods falling outside of this range are less effective. If the resistance of the discharge circuit is less than minimum the range factor must be correspondingly increased. For example, a discharge circuit having a resistance value of approximately six times the minimum value works best when the period of the magnetic field sinusoidal wave falls in the range of 1.67–2.0 times the time constant of the neurons to be stimulated.

Figure 11:
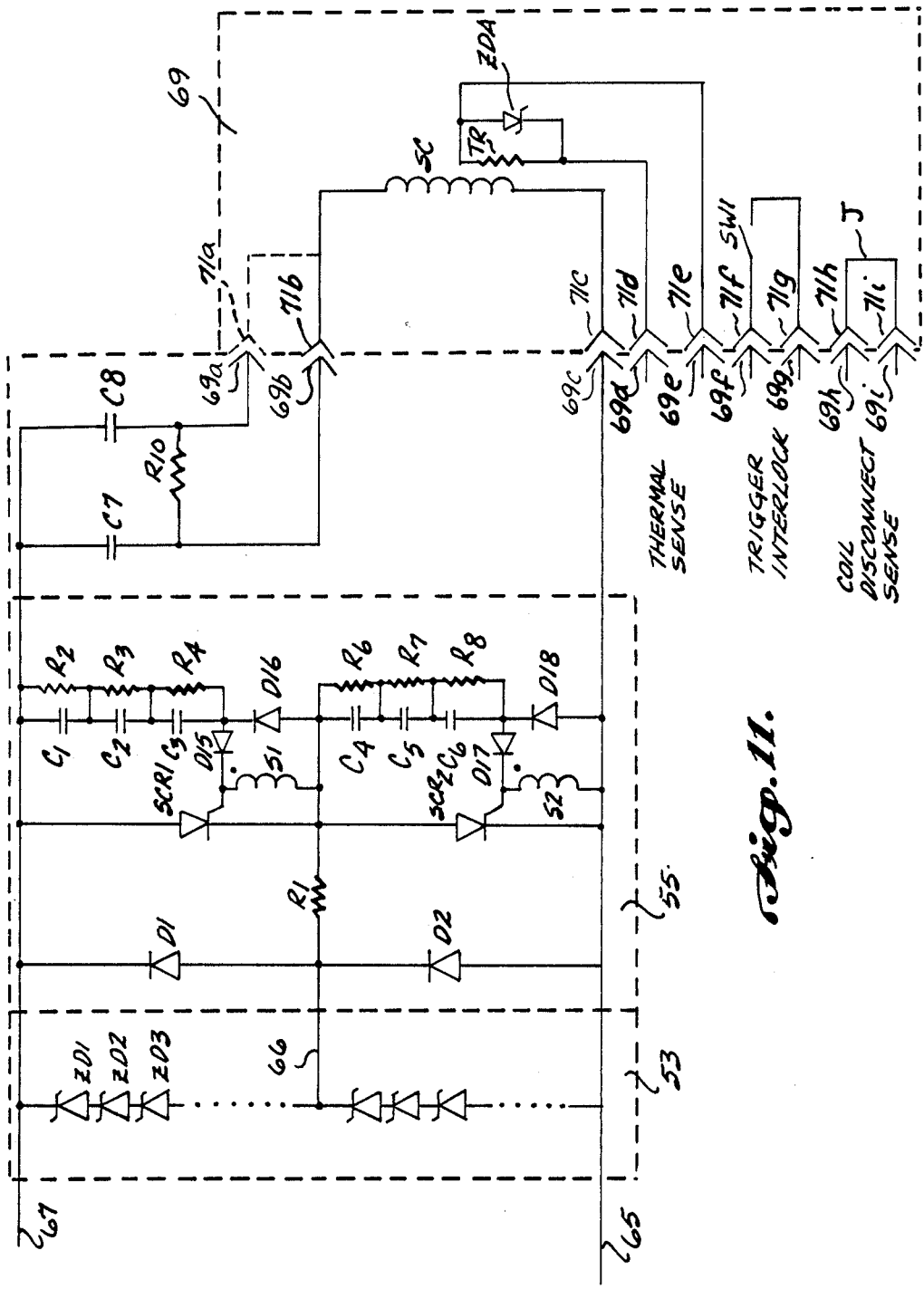
FIG. 11 is a schematic diagram illustrating an alternative power switch circuit suitable for use in the magnetic stimulator illustrated in FIG. 6; and, FIG. 12 is a waveform diagram that illustrates certain aspects of the operation of the magnetic stimulator illustrated in FIG. 6 that incorporates a power switch of the type illustrated in FIG. 11.

While the presently preferred apparatus and method of the invention are based on a single cycle mode of operation, multiple cycle modes of operation also fall within the scope of the invention. While some of the efficiency advantages obtainable by the preferred method and apparatus of the invention are lost when a multiple cycle mode of operation is undertaken, other efficiency advantages are retained. All that needs to be done to modify the apparatus of the invention so that it will operate in a multicycle mode is to modify the power switch 55 so that SCR1 and SCR2 are retriggered at the beginning of the second and subsequent cycles of operation rather than being quenched at the end of the first cycle of operation. FIG. 11 illustrates a modification that results in retriggering. The modification involves eliminating R5 and R9 and adding four diodes designated D15, D16, D17 and D18. The cathode of D15 is connected to the gate of SCR1 and the anode of D15 is connected to the junction between C3 and R4. The cathode of D16 is connected to the anode of D15 and the anode of D16 is connected to the junction of SCR1 and SCR2. The cathode of D17 is connected to the gate of SCR2 and the anode of D17 is connected to the junction between C6 and R8. The cathode of D18 is connected to the anode of D17 and the anode of D18 is connected to ground. While, configuration wise, C1, C2, C3, C4, C5, C6 and R2, R3, R4, R6, R7 and R8 remain as described above, obviously, the values of these components will vary in different embodiments of the invention. In essence, the values must be chosen so that the relative switching characteristics can be met, i.e., such that an adequate magnitude retriggering voltage is present on the gates of SCR1 and SCR2 at the beginning of second and subsequent cycles of operation in the case of the power switch illustrated in FIG. 11 and such that an inadequate magnitude retriggering the voltage is present on the gates of SCR1 and SCR2 at the beginning of the second cycle of operation in the case of the power switch illustrated in FIG. 7.

Figure 12:
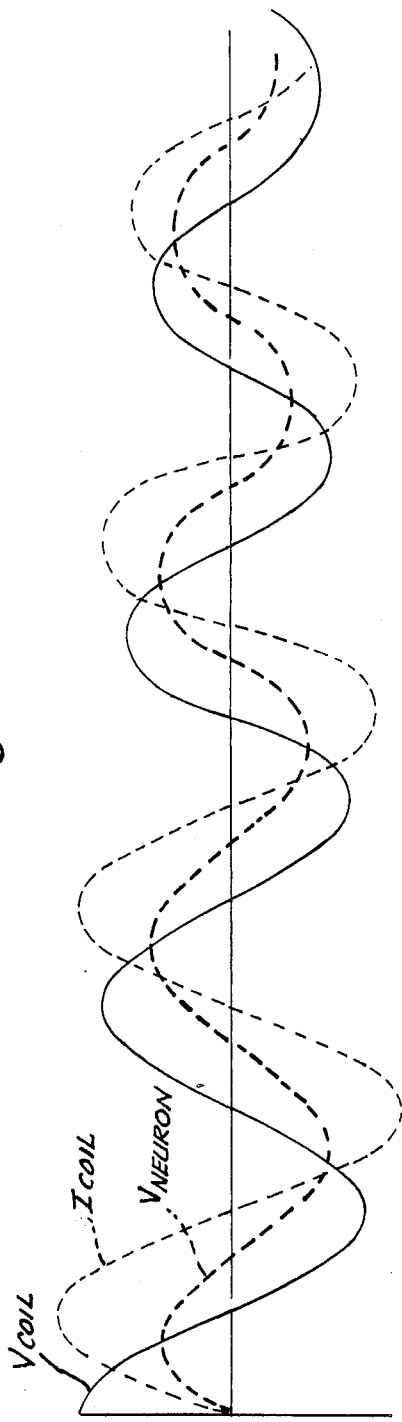

FIG. 12 illustrates the coil, voltage and current waveforms, and the depolarization neuron voltage generated by an embodiment of the invention of the type illustrated in FIG. 11. While the decaying capacitor voltage results in some loss of efficiency, some residual charge will remain on the capacitor bank when, after several cycles of operation, the voltage at the gates of SCR1 and SCR2 becomes inadequate to retrigger SCR1 and SCR2. Additional efficiency is achieved by maintaining the capacitor bank voltage at a level that will not create depolarization during the first quarter of the first cycle of operation, and choosing the magnetic field period to correspond to the time constant of the neurons to be depolarized in the manner described above.

As will be readily appreciated from the foregoing description, the invention provides an improved method of creating evoked responses and an improved magnetic stimulator. The method generally comprises the steps of: placing a magnetic stimulator coil on the skin of a patient overlying the neurons to be stimulated; and, creating a sinusoidal current flow in the coil that produces neuron depolarization, the magnitude of said current flow being inadequate to create neuron depolarization during the first quarter of the first cycle of current flow but adequate to create depolarization during the second and third quarter cycles. Preferably, the method includes the further step of terminating sinusoidal current flow in the coil after the first cycle is complete. The magnetic stimulator generally comprises: a highly efficient power supply; a power switch connected across the output of the power supply; and, a series circuit comprising a magnetic stimulator coil and a capacitor bank connected in parallel with the power switch. When the power switch is closed after the capacitor bank is charged, the capacitor bank discharge causes a sinusoidal current flow through the coil. Preferably, the apparatus of the invention also includes a connector block for connecting the magnetic stimulator coil to the capacitor bank and to the power switch so that selected ones of the capacitors that form said capacitor bank are connectable in series with a selected coil. Also, preferably, the power switch is triggerable and includes a mechanism for preventing retriggering in the absence of a trigger signal.

While preferred embodiments of the invention have been illustrated and described, it is to be understood that, within the scope of the appended claims, various changes can be made therein without departing from the invention.

The embodiments of the invention in which an exclusive property or privilege is claimed are defined as follows:

1. A method of stimulating the neural pathways of an organism, such as the human body, to create evoked potentials by depolarizing neurons forming part of the neural pathway to be stimulated, said method comprising the steps of:
    placing a stimulator coil on the surface of the organism in the region where a neural pathway is to be stimulated; and,
    energizing the stimulator coil by applying sinusoidal voltage to the coil that causes a high sinusoidal current to flow in the coil that causes the coil to generate a magnetic field that creates an electric field in the body of said organism in the region where a neural pathway is to be stimulated, said sinusoidal current flow being in phase quadrature with and lagging the sinusoidal voltage, the magnitude of said sinusoidal voltage being inadequate to create a current flow sufficient to generate a magnetic field that creates a neuron depolarizing electric field in the body of said organism during the first quarter of the first sinusoidal cycle of said applied voltage and adequate to generate a magnetic field that creates a neuron depolarizing electric field in the body of said organism during the second and third quarters of the first sinusoidal cycle of said applied voltage.

2. A method of stimulating the neural pathways of an organism as claimed in claim 1 including the further steps of:
    placing a pair of electrodes on the surface of said organism in the region where a neural pathway is to be stimulated; and,
    energizing said pair of electrodes by applying power to said electrodes that causes a current to flow through said organism from one electrode to the other electrode, said current flow creating an electric field that assists the electric field created by the magnetic field generated by said coil in creating a neuron depolarizing electric field in the body of said organism.

3. A method of stimulating the neural pathways of an organism as claimed in claim 2, wherein the electric field created by current flow between said electrodes is generated simultaneously with the electric field created by the magnetic field generated by said coil.

4. A method of stimulating the neural pathways of an organism as claimed in claim 3 wherein said electrodes and said coil are positioned on the surface of said organism such that one of said electrodes is surrounded by said coil.

5. The method of stimulating the neural pathways of an organism as claimed in claim 1 wherein said voltage is applied for a single sinusoidal cycle.

6. The method of stimulating the neural pathways of an organism as claimed in claim 5 wherein the frequency of said applied voltage is chosen such that the period of said single cycle falls in the range of 1.25 to 1.43 times the time constant of the neurons that form the neural pathway to be stimulated.

7. A method of stimulating the neural pathways of an organism as claimed in claim 6 including the further steps of:
    placing a pair of electrodes on the surface of said organism in the region where a neural pathway is to be stimulated; and,
    energizing said pair of electrodes by applying power to said electrodes that causes a current to flow through said organism from one electrode to the other electrode, said current flow creating an electric field that assists the electric field created by the magnetic field generated by said coil in creating a neuron depolarizing electric field in the body of said organism.

8. A method of stimulating the neural pathways of an organism as claimed in claim 7 wherein the electric field created by current flow between said electrodes is generated simultaneously with the electric field created by the magnetic field generated by said coil.

9. A method of stimulating the neural pathways of an organism as claimed in claim 8 wherein said electrodes and said coil are positioned on the surface of said organism such that one of said electrodes is surrounded by said coil.

10. A method of stimulating the neural pathways of an organism as claimed in claim 1 wherein the frequency of said applied voltage is chosen such that the period of the magnetic field that creates the depolarizing electric field falls in the range of 1.25 to 1.43 times the time constant of the neurons that form the neural pathway to be stimulated.

11. A method of stimulating the neural pathways of an organism as claimed in claim 10 including the further steps of:
    placing a pair of electrodes on the surface of said organism in the region where a neural pathway is to be stimulated; and,
    energizing said pair of electrodes by applying power to said electrodes that causes a current to flow through said organism from one electrode to the other electrode, said current flow creating an electric field that assists the electric field created by the magnetic field generated by said coil in creating a neuron depolarizing electric field in the body of said organism.

12. A method of stimulating the neural pathways of an organism as claimed in claim 11 wherein the electric field created by current flow between said electrodes is generated simultaneously with the electric field created by the magnetic field generated by said coil.

13. A method of stimulating the neural pathways of an organism as claimed in claim 12 wherein said electrodes and said coil are positioned on the surface of said organism such that one of said electrodes is surrounded by said coil.

14. A method of stimulating the neural pathways of an organism, such as the human body, to create evoked potentials by depolarizing neurons forming part of the neural pathway to be stimulated, said method comprising the steps of:
    placing a stimulator coil on the surface of the organism in the region where a neural pathway is to be stimulated; and,
    energizing the stimulator coil by applying at least one full wave of lightly damped sinusoidal voltage to the coil that causes a high sinusoidal current to flow in the coil, said sinusoidal current flow causing the coil to generate a magnetic field that creates a neuron depolarizing electric field in the body of said organism in the region where a neural pathway is to be stimulated, said sinusoidal current flow being in phase quadrature with and lagging, said sinusoidal voltage, the frequency of said applied voltage being chosen such that the period of said magnetic field that creates a neuron depolarizing electric field falls in the range of 1.25 to 1.43 times the time constant of the neurons that form the neural pathway to be stimulated.

15. A method of stimulating the neural pathways of an organism as claimed in claim 14 including the further steps of:
    placing a pair of electrodes on the surface of said organism in the region where a neural pathway is to be stimulated; and,
    energizing said pair of electrodes by applying power to said electrodes that causes a current to flow through said organism from one electrode to the other electrode, said current flow creating an electric field that assists the electric field created by the magnetic field generated by said coil in creating a neuron depolarizing electric field in the body of said organism.

16. A method of stimulating the neural pathways of an organism as claimed in claim 15 wherein the electric field created by current flow between said electrodes is generated simultaneously with the electric field created by the magnetic field generated by said coil.

17. A method of stimulating the neural pathways of an organism as claimed in claim 16 wherein said electrodes and said coil are positioned on the surface of said organism such that one of said electrodes is surrounded by said coil.

18. A method of stimulating the neural pathways of an organism as claimed in claim 14 wherein said voltage is applied for a single sinusoidal cycle.

19. A method of stimulating the neural pathways of an organism as claimed in claim 18 including the further steps of:
    placing a pair of electrodes on the surface of said organism in the region where a neural pathway is to be stimulated; and,
    energizing said pair of electrodes by applying power to said electrodes that causes a current to flow through said organism from one electrode to the other electrode, said current flow creating an electric field that assists the electric field created by the magnetic field generated by said coil in creating a neuron depolarizing electric field in the body of said organism.

20. A method of stimulating the neural pathways of an organism as claimed in claim 19 wherein the electric field created by current flow between said electrodes is generated simultaneously with the electric field created by the magnetic field generated by said coil.

21. A method of stimulating the neural pathways of an organism as claimed in claim 20 wherein said electrodes and said coil are positioned on the surface of said organism such that one of said electrodes is surrounded by said coil.

* * * * *

UNITED STATES PATENT AND TRADEMARK OFFICE
CERTIFICATE OF CORRECTION

PATENT NO. : 4,940,453

DATED : July 10, 1990

INVENTOR(S) : John A. Cadwell

It is certified that error appears in the above-identified patent and that said Letters Patent is hereby corrected as shown below:

Column 13, line 16, Delete "fiest" and insert therefor --first--

Signed and Sealed this

Twentieth Day of August, 1991

*Attest:*

HARRY F. MANBECK, JR.

*Attesting Officer*     Commissioner of Patents and Trademarks